United States Patent [19]

Lafon

[11] Patent Number: 4,983,599
[45] Date of Patent: Jan. 8, 1991

[54] 1-(4-AMINOPHENYL)-2-HEXAME-THYLENIMINOPROPANONE, AND THEIR USE IN THERAPY

[75] Inventor: Louis Lafon, Paris, France

[73] Assignee: Laboratoire L. Lafon, Maisons Alfort, France

[21] Appl. No.: 308,226

[22] Filed: Feb. 9, 1989

[30] Foreign Application Priority Data

Feb. 10, 1988 [FR] France ................... 8801565

[51] Int. Cl.$^5$ .................... A61K 31/55; C07D 295/10; C07D 295/12
[52] U.S. Cl. ..................................... 514/212; 540/610
[58] Field of Search ......................... 540/610; 514/212

[56] References Cited

FOREIGN PATENT DOCUMENTS 1240993 8/1988 Canada .
0174242 8/1985 European Pat. Off. .

*Primary Examiner*—Nicholas S. Rizzo
*Assistant Examiner*—Philip Datlow
*Attorney, Agent, or Firm*—Wegner, Cantor, Mueller & Player

[57] ABSTRACT

The present invention relates to 1-(4-aminophenyl-2)-hexamethyleniminopropanone and its pharmaceutically acceptable addition salts.

These products are useful in therapy on account of their antidepressant effects on the CNS and their immunological properties.

3 Claims, No Drawings

1-(4-AMINOPHENYL)-2-HEXAME- THYLENIMINOPROPANONE, AND THEIR USE IN THERAPY

The present invention relates to 1-(4-amino-phenyl)-2-hexamethyleniminopropanone and its pharmaceutically acceptable addition salts. It also relates to a process for preparing these products and their use in therapy.

It is known that 1-(aminophenyl)-2-aminopropanone derivatives of formula

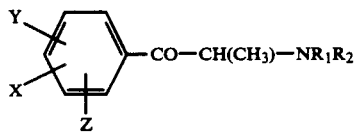

in which
X is $NH_2$,
Y is a hydrogen or halogen atom,
Z is a hydrogen or halogen atom,
$R_1$ is a $C_1$–$C_4$ alkyl group or a $C_3$–$C_5$ cycloalkyl group,
$R_2$ is a hydrogen atom or a $C_1$–$C_4$ alkyl group,
$R_1$ and $R_2$, taken together, can form, with the nitrogen atom to which they are attached, a 5- to 7-membered N-heterocyclic group capable of including a second hetero atom chosen from N, O and S and capable of being substituted, the said heterocyclic group $NR_1R_2$ being chosen from the group comprising pyrrolidino, morpholino, thiomorpholino, piperidino, hexamethylenimino, piperazino, 4-methylpiperazino,4-(2-hydroxyethyl)piperazino,4-phenylpiperazino and 4-(p-chlorophenyl)piperazino groups; and their addition salts, have already been recommended in the past as agents with an antidepressant effect on the central nervous system (CNS). It is also known that, among the compounds of formula $I_o$ above, only a few products display, in addition, beneficial cardiovascular and/or immunological properties. See, for this purpose, Patent EP-B-No. 0,174,242.

According to the invention, new products belonging to the family of 1-(aminophenyl)-2-aminopropanone derivatives are proposed, namely 1-(4-aminophenyl)-2-hexamethyleniminopropanone and its addition salts.

A process for preparing the said 1-(4-aminophenyl)-2-hexamethyleniminopropanone is also proposed, this free base and its pharmaceutically acceptable addition salts being especially useful in therapy on account of their antidepressant effects on the one hand, and their immunomodulatory effects on the other hand.

1-(4-Aminophenyl)-2-hexamethyleniminopropanone is admittedly included in the general formula of the Patent EP-B-0,174,242, although it is not specifically exemplified. It displays antidepressant effects like all the compounds described in EP-B-0,174,242, but differs from its analogues which are closest from the structural standpoint in that it possesses beneficial immunomodulatory effects enabling it to be used as an immunostimulatory agent. See the results of the comparative tests given below.

The new 1-(aminophenyl)-2-aminopropanone derivatives according to the invention are characterized in that they are selected from the group consisting of:

(a) 1-(4-aminophenyl)-2-hexamethyleniminopropanone of structural formula

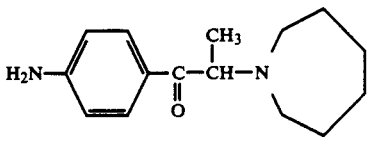

(b) and its pharmaceutically acceptable addition salts.

Pharmaceutically acceptable addition salts are understood here to mean salts which give the biological properties of the free base without having adverse effects. These salts can be the salts obtained by reaction of the free base of formula I with an inorganic or organic acid, or can be ammonium salts. Among acids which are usable for salifying the free base of formula I, there may be mentioned, in particular, hydrochloric, hydrobromic, acetic, formic, propionic, oxalic, fumaric, maleic, succinic, benzoic, cinnamic, mandelic, citric, malic, tartaric, aspartic, glutamic, methanesulphonic and p-toluenesulphonic acids. Among compounds enabling ammonium salts to be obtained, $CH_3I$ and $CH_3Cl$ may be mentioned in particular. Generally speaking, the addition salts with an acid, such as, in particular, the dihydrochloride, are preferred to the ammonium salts.

The compound of formula I may be prepared according to a method which is known per se, by application of traditional reaction mechanisms. It can, in particular, be synthesized according to one of the appropriate working methods described in EP-B-No. 0,174,242.

The process which is recommended here consists in hydrolysing the corresponding 4-acetamido derivative in a strong acid medium. This process is characterized in that 0.10 to 0.20 mole of 1-(4-acetylaminophenyl)-2-hexamethyleniminopropanone is reacted with 100 to 300 ml of 4 N of HCl acid for at least 0.5 h at the refluxing temperature of the reaction medium.

1-(4-Acetylaminophenyl)-2-hexamethyleniminopropanone may itself be obtained by the reaction in aqueous medium of α-chloro-p-acetamidopropiophenone with an excess of hexamethylenimine.

The compound of formula I and its pharmaceutically acceptable addition salts display beneficial therapeutic properties. They act as antidepressant means; they display, in addition, stimulatory effects on the CNS, which is not the case with all the products described in EP-B-No. 0,138,714.

However, the importance of a compound of formula I and its pharmaceutically acceptable addition salts resides mainly in the fact that they display, apart from the stimulatory effects on the CNS, immunostimulatory effects.

Many studies have shown that psychological stimuli such as stress and depression can have a profound influence on a large number of physiological processes. Thus, exposure to stress-creating situations is accompanied by a decrease in the immunological functions, which leads to infectious diseases. The existence of such a link between the mind and immunity and vice versa constitutes the basis of the therapeutic importance of the compounds according to the invention, which possess both antidepressant and stimulant properties with respect to the central nervous system and immunostimulatory effects. They hence find special importance in the treatment of depressive states and of stress-inducing situations associated with infectious diseases.

According to the invention, a therapeutic composition is recommended which is characterized in that it contains at least one derivative selected from the compound of formula I and its pharmaceutically acceptable addition salts, in combination with a physiologically acceptable excipient.

Naturally, in such a composition, the active principle, namely the compound of formula I or one of its pharmaceutically acceptable salts, is present in a pharmaceutically effective amount.

According to the invention, the use is recommended of a substance selected from the group consisting of 1-(4-aminophenyl)-2-hexamethyleniminopropanone and (ii) its pharmaceutically acceptable addition salts, for the production of a medicinal product with an antidepressant effect on the CNS, intended for use in human therapy in relation to depression and depressive states.

According to the invention, the use is also recommended of a substance selected from the group consisting of 1-(4-aminophenyl)-2-hexamethyleniminopropanone, and its pharmaceutically acceptable addition salts, for the production of an immunostimulatory medicinal product intended for use in human therapy in the case where an immunostimulation is required.

Other advantages and characteristics of the invention will be better understood on reading an example which follows of preparation and of results of pharmacological tests, all these data being in no way limiting but given by way of illustration.

EXAMPLE

Preparation of 1-(4-aminophenyl)-2-hexamethylenimiopropanone dihydrochloride (Code No. CRL 41 405)

(a) Preparation of α-chloro-o-acetamidopropiophenone 118 g (0.93 mole) of α-chloropropionyl chloride are introduced in the space of 1 h 30 min into a mixture of 69.2 g (0.50 mole) of acetanilide and 205 g (1.50 mole) of aluminium chloride in 525 ml of carbon disulphide, and the mixture is heated under reflux for 1 h. The supernatant is decanted and the residue hydrolysed with 1,900 ml of ice-cold water and 385 ml of 4 N hydrochloric acid.

The precipitate is isolated by filtration and taken up with benzene which is distilled off azeotropically in a Dean and Stark apparatus. After treatment of the hot solution with CXA charcoal and cooling, 102.4 g of a pale beige powder are isolated.

M.p.$_{inst.}$ (Kofler) 120° C.

Yield = 90.82%.

(b) Preparation of 1-(4-acetylaminophenyl)-2-hexamethyleniminopropanone hydrochloride 56 g (0.248 mole) of the product obtained in a) and 280 ml (2.48 moles) of hexamethylenimine are stirred for 3 hours at room temperature in 300 ml of water. The reaction medium is diluted with 500 ml of water, and the insoluble material extracted with ethyl acetate, which is washed copiously with water. The organic phase is dried over dry sodium sulphate and then treated with ethanolic hydrogen chloride.

The precipitate obtained is purified by two successive crystallizations in absolute ethanol and water to give 59 g of a white powder which is soluble in water to the extent of 3%.

M.p. ≃ 210° C. (d)

Yield = 73.3%

Total yield = 66.6%.

(c) Preparation of 1-(4-aminophenyl)-2-hexamethyleniminpropanone dihydrochloride A solution of 52 g (0.16 mole) of 1-(4-acetylaminophenyl)-2-hexamethyleniminopropanone hydrochloride in 250 ml of 4 N HCl acid is heated under reflux for 1 h. The reaction medium is then treated with carbon black ("charcoal 3S") and, after filtration, the filtrate is evaporated under reduced pressure to take it to dryness. The oily residue thereby obtained is taken up with benzene, which is distilled off azeotropically by means of a Dean and Stark apparatus to give, after filtration of the precipitate formed, 51.5 g of product in the form of a white powder with green glints, which is soluble in water to the extent of 400 g/l.

M.p.$_{inst.}$ (Kofler) approximately 160° C.

Yield = close to 100%.

The results of the tests which were undertaken with CRL 41 405 according to the invention are summarized below.

A. IMMUNOLOGICAL STUDY

The immunological study was carried out according to several protocols in order to assess, by comparative tests, the possible immunomodulatory properties of CRL 41 405 and its analogues.

The so-called test of lytic plaque-forming cells described by A. J. Cunningham et al. ("Further improvements in the plaque technique for detecting single antibody forming cells"), Immunology 14, pages 599–601, (1968), on the one hand, and the so-called test of intensity of delayed hypersensitivity to sheep red cells described by T. E. Miller et al. ("Immunopotentiation with BCG II modulation of the response to sheep blood cells"), Journal of the National Cancer Institute 51 (No. 5), pages 1669–1676, (1973), on the other hand, were used in particular.

(1) The test of lytic plaque-forming cells (or IgM PFC).

This test explores humoral immunity. Four days after immunization with a T-dependant antigen (in this case sheep red cells), the number of spleen cells expressing a direct IgM antibody response is counted. The mice used for this purpose are conventional OF$_1$ female mice, examples of specific pathogenic organisms, weighing from 20 to 30 g, and distributed according to a control batch of 14 animals and batches of 7 animals each per dose and per test product administered orally on the same day as the antigen. An index of activity I is calculated for each dose of product according to the relationship:

$$I = \frac{\text{mean of lyses per spleen of the treated mice}}{\text{mean of lyses per spleen of the control mice}}$$

This test is carried out at least twice for each dose (0.001; 0.01; 0.1; 10; and 100 mg/kg) of test product, and a statistical study is undertaken by means of Student's t test after analysis of variance on the number of lyses per spleen.

It is observed that CRL 41 405 displays an activity at a dose of 1 mg/kg and above, and that the index of activity increases with the dose to attain the value I = 1.58 at a dose of 100 mg/kg P.O.

By way of comparison, 1-(4-aminophenyl)-2-piperidinopropanone dihydrochloride (CRL 41 241), described in EP-B-No. 0,174,242 gives a reaction only at a dose of 100 mg/kg.

(2) Test of intensity of delayed hypersensitivity to sheep red cells

This is a technique of exploration of cellular immunity. The test compound is administered either orally if it is insoluble, or (as is the case in the present instance) subcutaneously in the foot pad when it is water-soluble, the administration of the said compound taking place three days before immunization (by subcutaneous administration of sheep red cells in the plantar pad) of conventional OF female mice distributed according to a control batch of 10 animals and batches of 5 animals each per dose and per test product.

This test is carried out at least twice for each dose (0.001; 0.01; 0.1; 10; and 100 mg/kg) of test product, and a statistical study is undertaken as described above. The change in thickness of the plantar pad is measured in order to determine the percentage increase in thickness of the plantar pad. An index of activity is then calculated according to the relationship $$I_{D5} = T/T_o$$

where
T = T mean percentage increase in thickness of the plantar pad of the treated mice; and
$T_o$ = mean percentage increase in thickness of the plantar pad of the control mice.

It is found that CRL 41 405 according to the invention gives a positive response at all doses used, to attain the value $I_{D5}$ = 1.77 at a dose of 100 mg/kg S. C.

All these results demonstrate that CRL 41 405 (i) is an immunomodulatory product and (ii) acts, more specifically, as an immunostimulatory substance.

NEUROPSYCHOPHARMACOLOGICAL STUDY

During the study of the neuropsychopharmacological properties, CRL 41 405 dissolved in distilled water was administered intraperitoneally in a volume of 20 ml/kg in male mice and 5 ml/kg in male rats.

The pH of the aqueous solution to be injected varies with the concentration of CRL 41 405, as shown in the table below.

TABLE

| Concentration of CRL 41 405 in the aqueous administration solution | pH of the aqeuous administration solution |
|---|---|
| 50 g/l | 1.5 |
| 1.6 g/l | 2.5 |
| 0.8 g/l | 3.5 |
| 0.2 g/l | 4.5 |
| 0.05 g/l | 5.5 |

I. TOXICITY

In male mice the $LD_o$ (maximal non-lethal dose) of CRL 41 405 administered intraperitoneally is more than 64 mg/kg, the $LD_{60}$ (lethal dose for 60% of the animals treated) is of the order of 128 mg/kg and the $LD_{100}$ (minimal lethal dose for all the animals treated) is less 256 mg/kg.

II. OVERALL BEHAVIOUR AND REACTIVITIES

Batches of three animals are observed before and then 0.25 h, 0.50 h, 1 h, 2 h, 3 h and 24 h after the administration of CRL 41 405. The observations are as follows:

(1) In mice
at a dose of 0.5 mg/kg:
  behaviour and reactivities substantially comparable to those of the control batch;
at doses of 2 mg/kg and 8 mg/kg:
  excitation, the maximal intensity being manifested 2 h after administration of CRL 41 405;
at a dose of 16 mg/kg:
  excitation, the maximal intensity being manifested 2 to 2.5 h after administration of CRL 41 405;
  exophthalmos;
at a dose of 32 mg/kg:
  exophthalmos for 1 h,
  excitation lasting 2 to 2.5 h, accompanied by stereotypies for 0.5 h,
  an increase in the fear reaction and an increase in the reactivity to touch,
  hypothermia for 2 h ($-2°$ C., 30 minutes after administration of CRL 41 405); and
  moderate mydriasis for 3 h;
at a dose of 64 mg/kg:
  excitation for 5 h,
  exophthalmos,
  convulsions,
  no mortality.

(2) In rats of 0.25 mg/kg, 1 mg/kg and 4 mg/kg:
at doses of 0.25 mg/kg, 1 mg/kg and 4 ;1 mg/kg:
  behaviour, reactivities, a change in rectal temperature and in the pupil diameter substantially comparable to those of the control batch;
at a dose of 16 mg/kg:
  excitation for 1 h,
  stereotyped movements,
  mydriasis for 2 h.

III. OTHER TESTS

The tests carried out according to the working procedures described in EP-B-No. 0,174,242 (i.e. interaction with apomorphine, interaction with amphetamine, interaction with reserpine, interaction with oxotremorine, action on the four-plates test, traction and electric shock, action on spontaneous motility, action on intergroup aggressiveness, action with respect to motility reduced by familiarization with the enclosure, action with respect to motility reduced by hypoxic attack, action with respect to asphyxic anoxia, interaction with barbital, action on "behavioural despair") enabled it to be demonstrated that CRL 41 405 displays in its neuropsychopharmacological profile the following effects:

antidepressive, judged by the antagonism of apomorphine-, reserpine- or oxotremorine-induced hypothermia on the one hand, and by the decrease in the period of so-called despair immobility on the other hand; and CNS-stimulatory, both in rats (presence of stereotyped movements, potentiation of amphetamine-induced stereotypies) and in mice (antagonism of barbital-induced sleep, resumption of motor activity in animals familiarized with their enclosure, improvement in motor recovery after hypobaric anoxia and moderate increase in spontaneous motility).

CRL 41 405 displays, in addition, signs of peripheral alpha-adrenergic stimulation (mydriasis, moderate antagonism of reserpine-induced ptosis and antagonism of oxotremorine-induced tremor); nevertheless, according to these tests, CRL 41 405 appears to be a very weak means of producing α-adrenergic stimulation.

I claim.

1. A compound selected from the group consisting of 1-(4-aminophenyl)-2-hexamethyleniminopropanone and a pharmaceutically acceptable addition salt thereof.

2. 1-(4-aminophenyl)-2-hexamethyleniminopropanone dihydrochloride.

3. A process for the stimulation of the immunological functions in a human in need thereof, comprising administering to aid human a compound selected from the group consisting of 1-(4-aminophenyl)-2-hexamethyleniminopropanone and a pharmaceutically acceptable addition salt thereof:

* * * * *